United States Patent
Kozlowski

(10) Patent No.: US 9,259,296 B2
(45) Date of Patent: Feb. 16, 2016

(54) SEQUENTIAL MODULES FOR COMPUTER AIDED BRACKETING SYSTEMS AND ASSOCIATED METHODS AND DEVICES

(71) Applicant: Jeffrey T. Kozlowski, New London, CT (US)

(72) Inventor: Jeffrey T. Kozlowski, New London, CT (US)

(73) Assignee: Jeffrey T. Kozlowski, New London, CT (US)

( * ) Notice: Subject to any disclaimer, the term of this patent is extended or adjusted under 35 U.S.C. 154(b) by 18 days.

(21) Appl. No.: 14/054,399

(22) Filed: Oct. 15, 2013

(65) Prior Publication Data

US 2014/0106289 A1    Apr. 17, 2014

Related U.S. Application Data

(60) Provisional application No. 61/713,902, filed on Oct. 15, 2012.

(51) Int. Cl.
| | | |
|---|---|---|
| A61C 7/00 | (2006.01) | |
| A61C 7/14 | (2006.01) | |
| A61C 7/20 | (2006.01) | |

(52) U.S. Cl.
CPC ............... *A61C 7/146* (2013.01); *A61C 7/002* (2013.01); *A61C 7/20* (2013.01); *A61C 2202/00* (2013.01)

(58) Field of Classification Search
CPC ............... A61C 7/002; A61C 2007/00; A61C 2007/004; A61C 2007/002
USPC .......................................................... 433/24
See application file for complete search history.

(56) References Cited

U.S. PATENT DOCUMENTS

| | | | |
|---|---|---|---|
| 5,533,895 A | | 7/1996 | Andreiko et al. |
| 6,632,089 B2 * | | 10/2003 | Rubbert et al. ................ 433/24 |
| 2003/0027098 A1 * | | 2/2003 | Manemann et al. ........... 433/24 |
| 2004/0073417 A1 | | 4/2004 | Rubbert et al. |
| 2004/0214128 A1 * | | 10/2004 | Sachdeva ................ A61C 7/00 433/24 |
| 2010/0190125 A1 | | 7/2010 | Lee |
| 2011/0217667 A1 | | 9/2011 | Groscurth et al. |

FOREIGN PATENT DOCUMENTS

WO        WO 01-80761        11/2001

OTHER PUBLICATIONS

International Search Report and Written Opinion received in Patent Cooperation Treaty Application No. PCT/US2013/065035, dated Jan. 20, 2014, 13 pages.

* cited by examiner

*Primary Examiner* — Ralph Lewis
(74) *Attorney, Agent, or Firm* — Haynes & Boone, LLP

(57) ABSTRACT

A system providing transitional bracket and transfer jig modules that have been custom designed to address a rotated or partially erupted tooth in advance of applying a computer aided bracketing system to the tooth. The transfer jigs and brackets are used until the problem tooth is moved into a position that will allow positioning of the "ideal" bracket. Once the ideal brackets are position, the treatment plan can proceed as it would with existing systems to reach the final ideal position. The transitional modules are integrated into the customized treatment plan such that the orthodontist just follows the digitized plan, including correction of misaligned teeth. The computer system that assists with defining the treatment plan takes into account the starting position of the teeth and can adjust the plan, as well as use of transitional brackets, to accommodate many more patients that have one or more problem teeth needing correction.

20 Claims, 16 Drawing Sheets

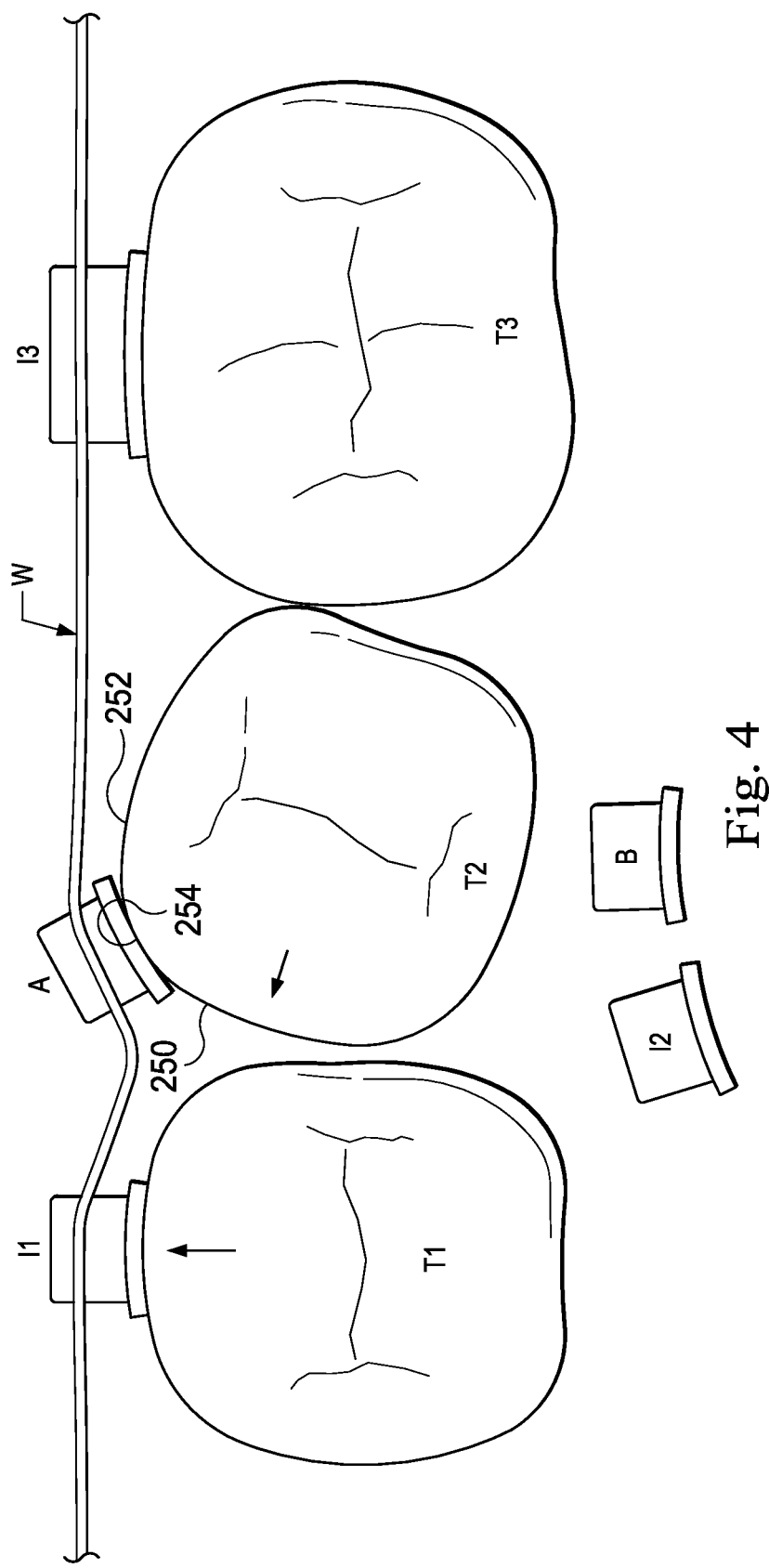

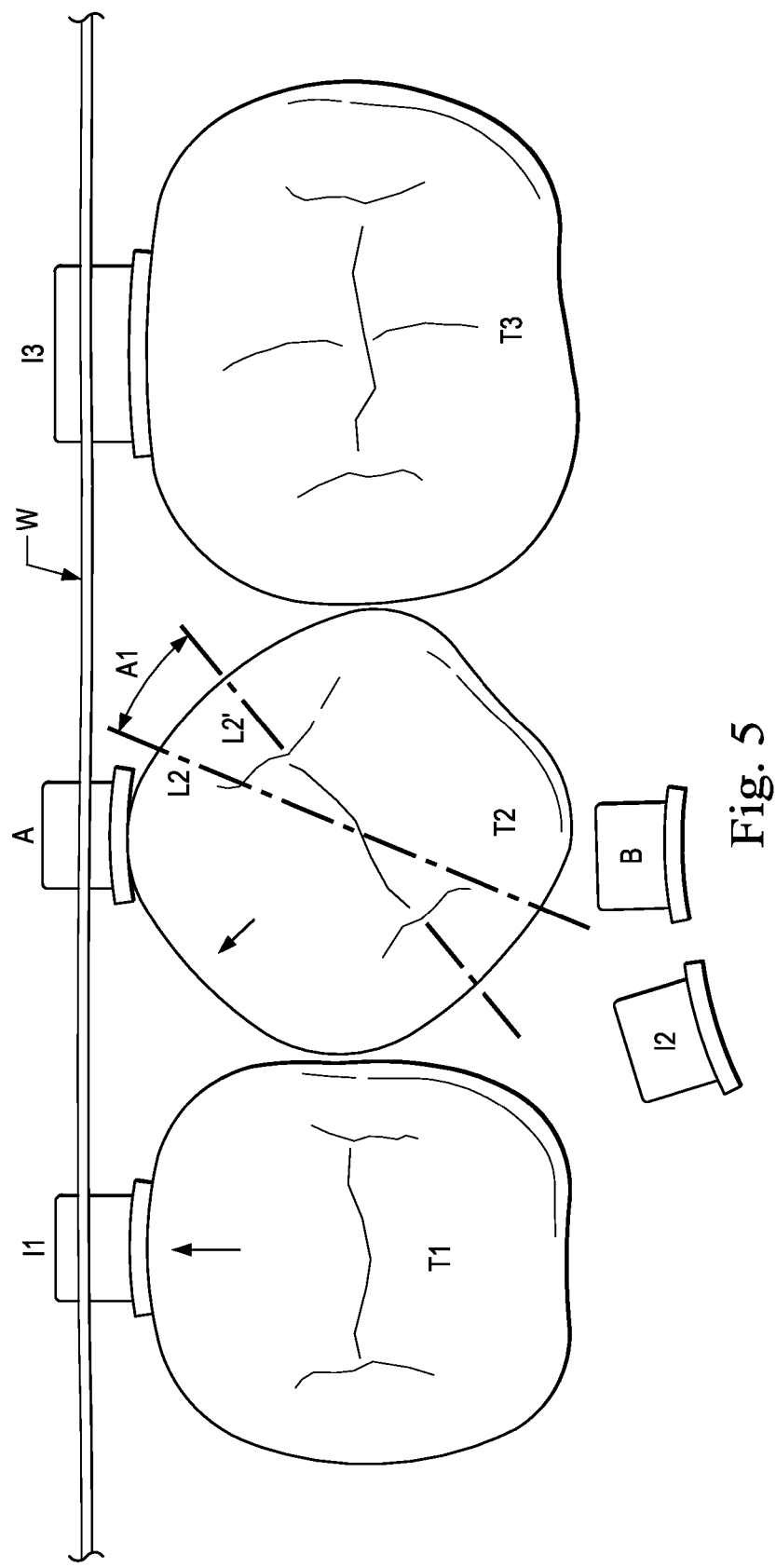

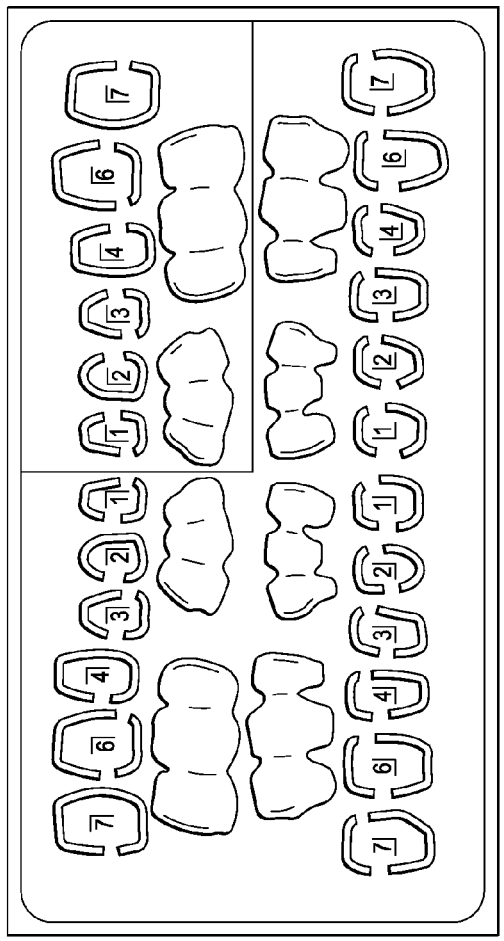
Fig. 12
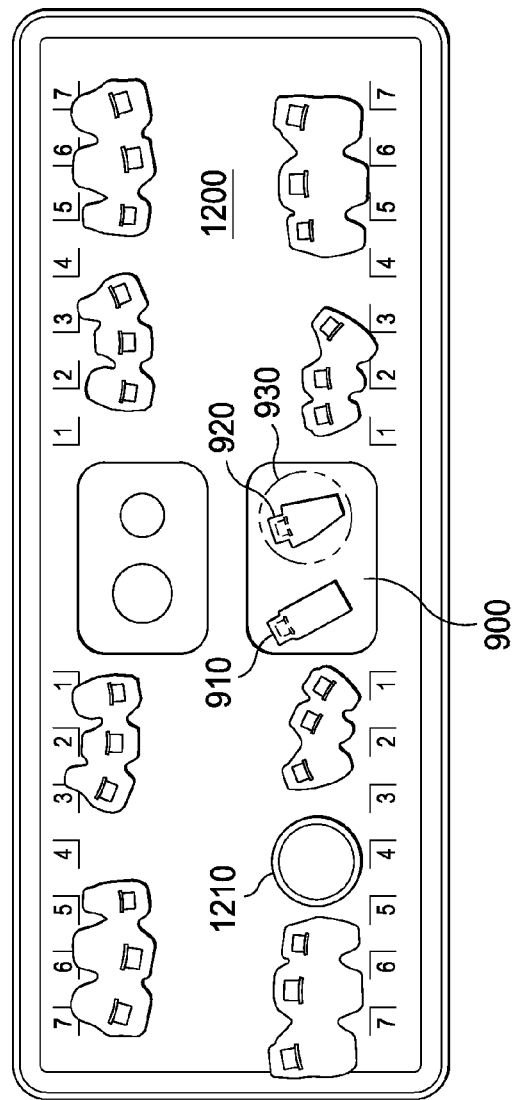

SEQUENTIAL MODULES FOR COMPUTER AIDED BRACKETING SYSTEMS AND ASSOCIATED METHODS AND DEVICES

CROSS REFERENCE TO RELATED APPLICATION

The present application claims priority to and the benefit of U.S. Provisional Patent Application No. 61/713,902, filed Oct. 15, 2012, which is hereby incorporated by reference herein in its entirety.

BACKGROUND

Existing digital orthodontic systems utilize digitized images of the teeth to generate a customized treatment system of brackets, transfer jigs and wires. This system assumes that all of the custom designed brackets and transfer jigs can be placed on the facial or labial surface of the tooth. Unfortunately, for some patients a tooth may be rotated or otherwise malpositioned such that the facial surface is not facing outward or the tooth has not fully erupted through the gums. In these situations, the orthodontist must first recognize the problem condition and then use manual techniques to derotate or otherwise move the tooth so that the "customized" system can then be placed. Given the cost of such customized systems, it then becomes less desirable to use a customized orthodontic set because the orthodontist must use traditional techniques in addition to the customized versions.

The devices, systems, and methods disclosed herein overcome one or more of the deficiencies of the prior art.

SUMMARY

In a first aspect, the present disclosure provides a method for computer aided tooth alignment correction. The disclosed method includes determining sequential brackets and placement locations on the same tooth to accomplish a computer aided treatment plant. In one aspect, the method can include receiving digital information regarding initial teeth positions; determining desired final teeth positions and a treatment plan of ideal brackets, jigs and wires for achieving the final teeth positions; identifying whether there will be interferences between at least one of the ideal brackets, jigs, wires, teeth and gums; and upon identification of interferences, generating one or more sequential treatment modules addressing the identified interference. In a further aspect, the method further includes packaging the ideal brackets and jigs along with the sequential treatment module.

In a further embodiment, the present disclosure provides a tooth correction system that can be applied in a sequential manner to the same tooth. In one aspect, the correction system includes a first transfer jig having an occlusal surface configured to engage the occlusal surface of a tooth and a mounting surface having a bracket holding feature, the mounting surface configured for orientation with a first surface of the tooth having a first plane offset at a first acute angle from the tooth longitudinal axis. In another aspect, the system includes a second transfer jig configured to engage the occlusal surface of the tooth and having a second mounting surface having a second bracket holding feature, the second mounting surface configured for orientation with a second surface of the tooth having a second plane offset at a second acute angle from the tooth longitudinal axis. Still further, the system can include a plurality of ideal transfer jigs in addition to the first transfer jig and the second transfer jig, each of the plurality of ideal transfer jigs adapted for engaging different teeth within a patient's mouth and having a mounting surface having a bracket holding feature, the mounting surface configured for orientation with a facial surface of the tooth.

In yet a further aspect, the present disclosure contemplates a tooth correction kit comprising a plurality of tooth brackets and a plurality of transfer jigs for positioning the tooth brackets at a predetermined location on the teeth, wherein at least two of the tooth brackets are designed for sequential placement on the same tooth. The tooth correction kit can further included at least two transfer jigs configured for engaging the same tooth at two different angular positions with respect to the longitudinal axis of the tooth.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number or character. The characteristics, attributes, functions, interrelations ascribed to a particular element in one location apply to those elements when referred to by the same reference number or character in another location unless specifically stated otherwise.

The figures referenced below are drawn for ease of explanation of the basic teachings of the present disclosure only; the extensions of the figures with respect to number, position, relationship, and dimensions of the parts to form the following embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

The following is a brief description of each figure used to describe the present invention, and thus, is being presented for illustrative purposes only and should not be limitative of the scope of the present invention.

Figure 1:
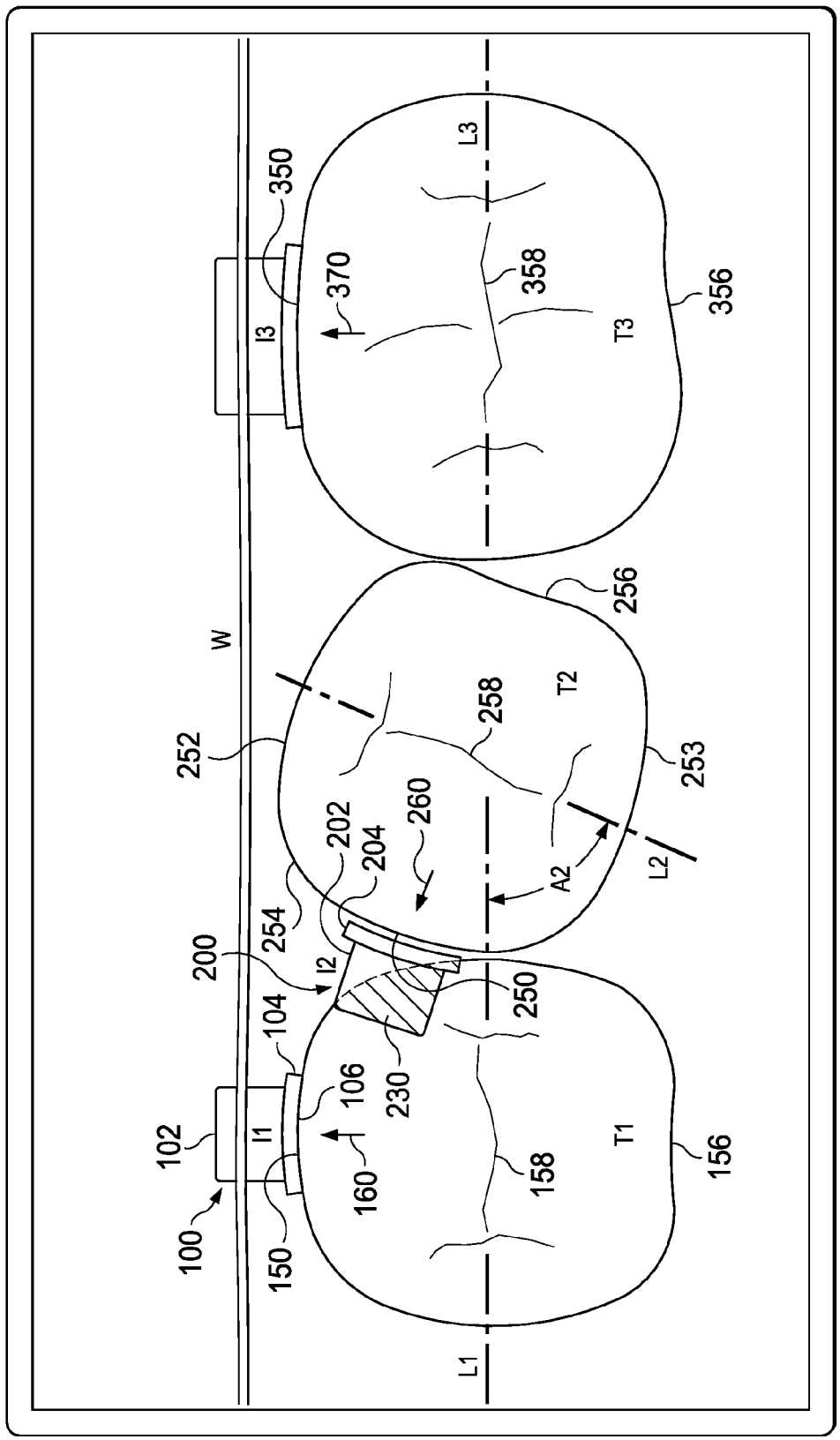

FIG. 1 is a stylized view of a portion of a computer aided treatment plan according to a prior art system.

Figure 2:
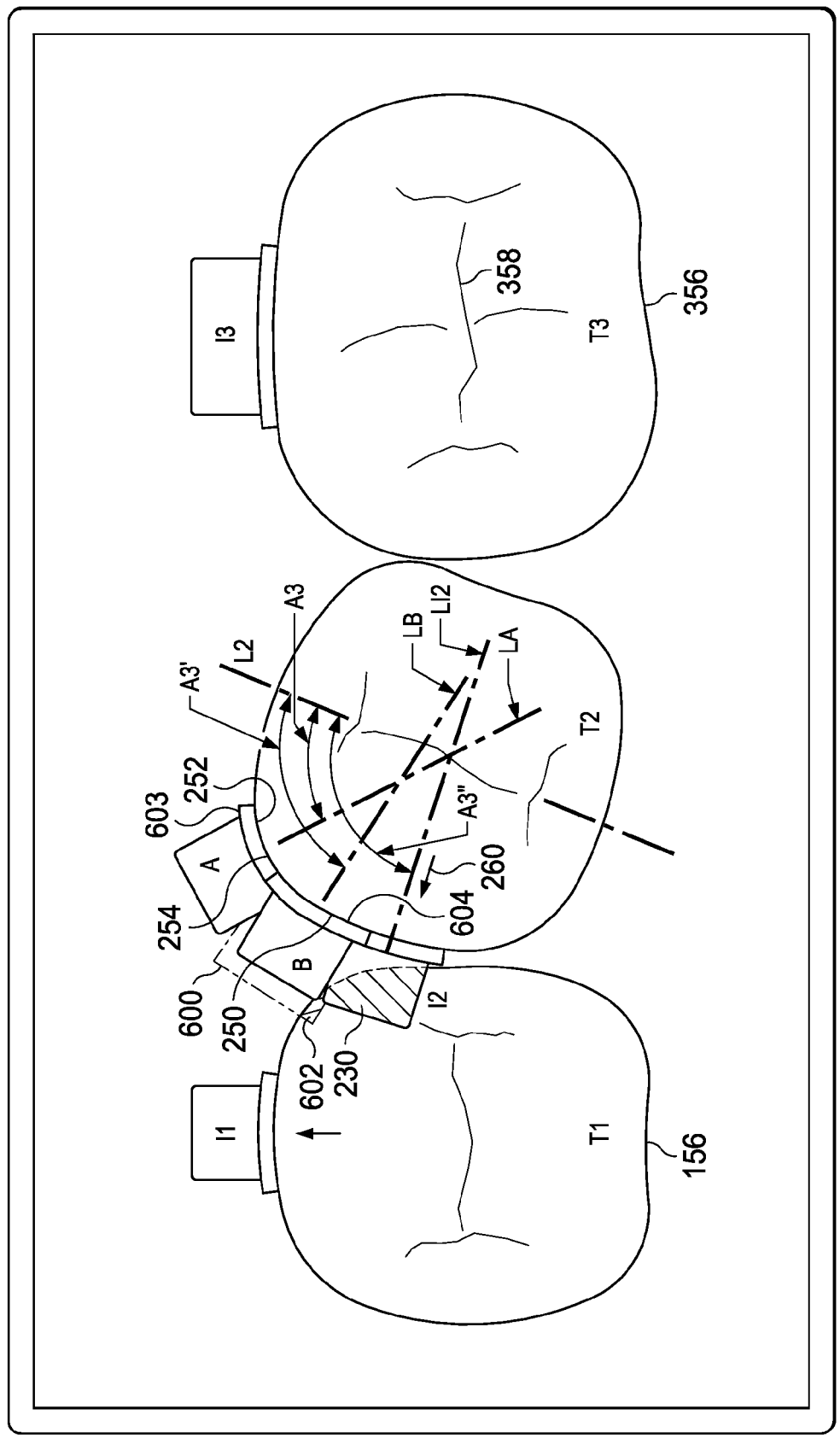

FIG. 2 is a stylized view of a portion of a computer aided treatment plan according to an as aspect of the present disclosure.

Figure 3A:
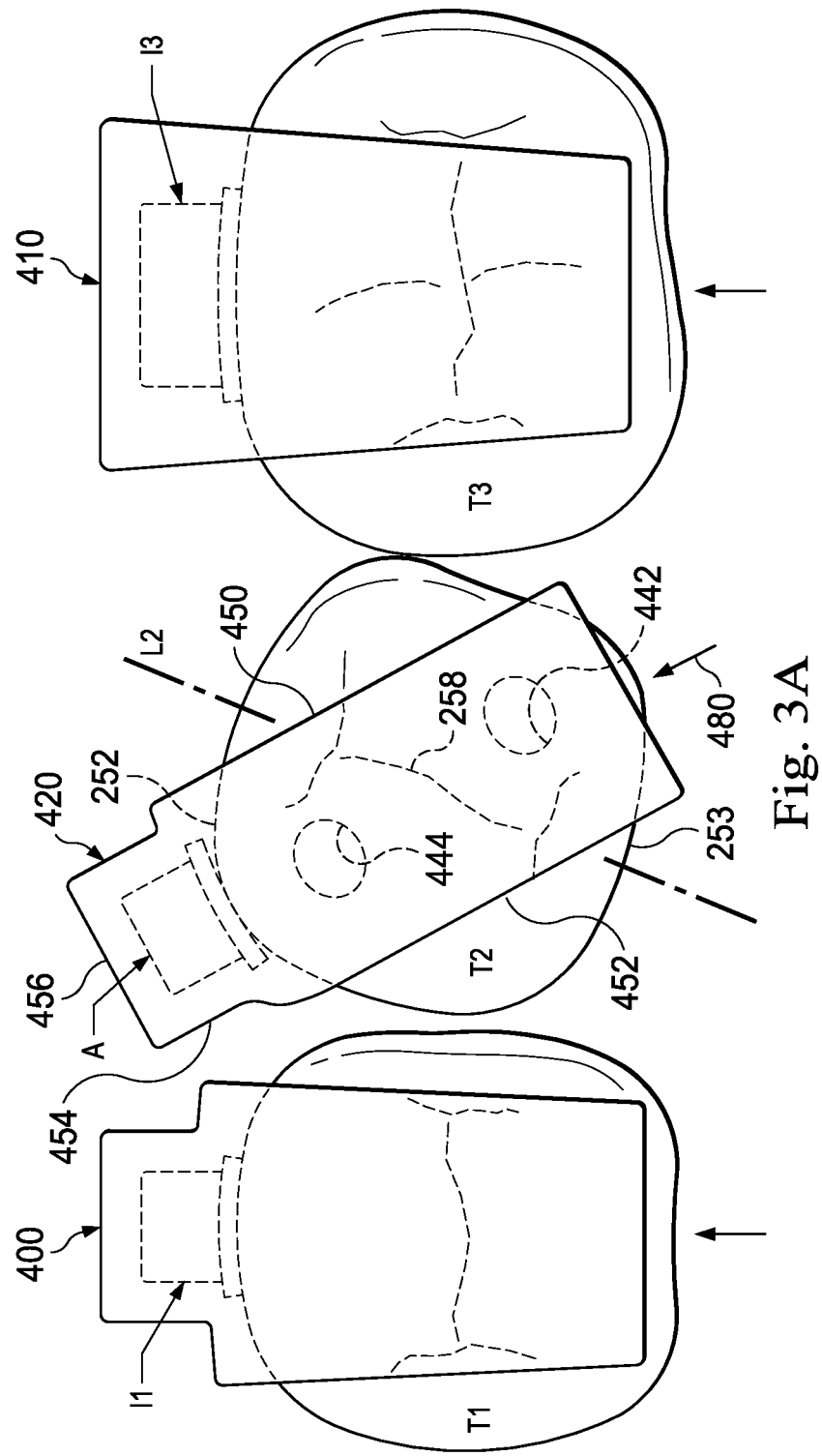

FIG. 3A is top view of a transfer jig and bracket system being applied to a series of teeth.

Figure 3B:
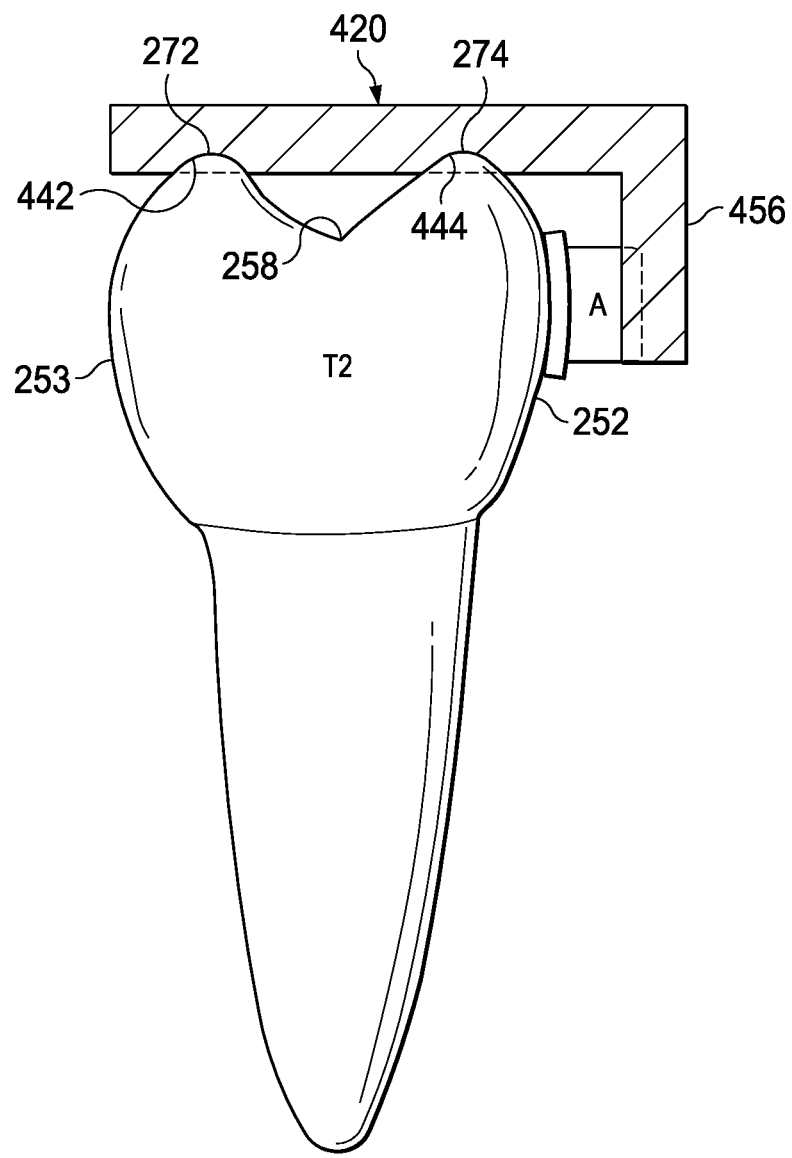

FIG. 3B is a partial cross sectional side view of the transitional jig and bracket of FIG. 3A.

FIG. 4 is a top view of the transitional bracket of FIG. 3A bonded to the tooth and attached to the wire in an initial position.

FIG. 5 is a top view of the transitional bracket of FIG. 3A bonded to the tooth and attached to the wire in a first transitional position.

Figure 6A:
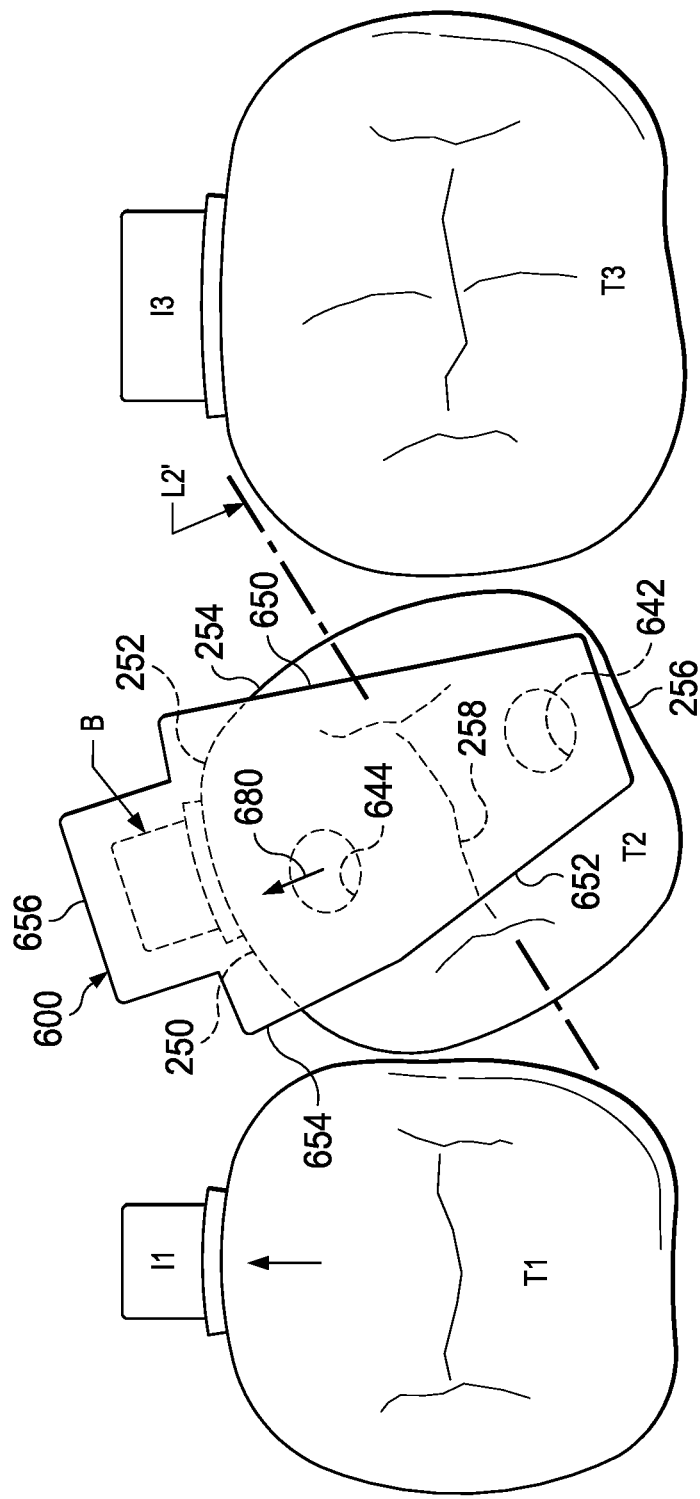

FIG. 6A is top view of a second transfer jig and bracket system being applied to the series of teeth.

Figure 6B:
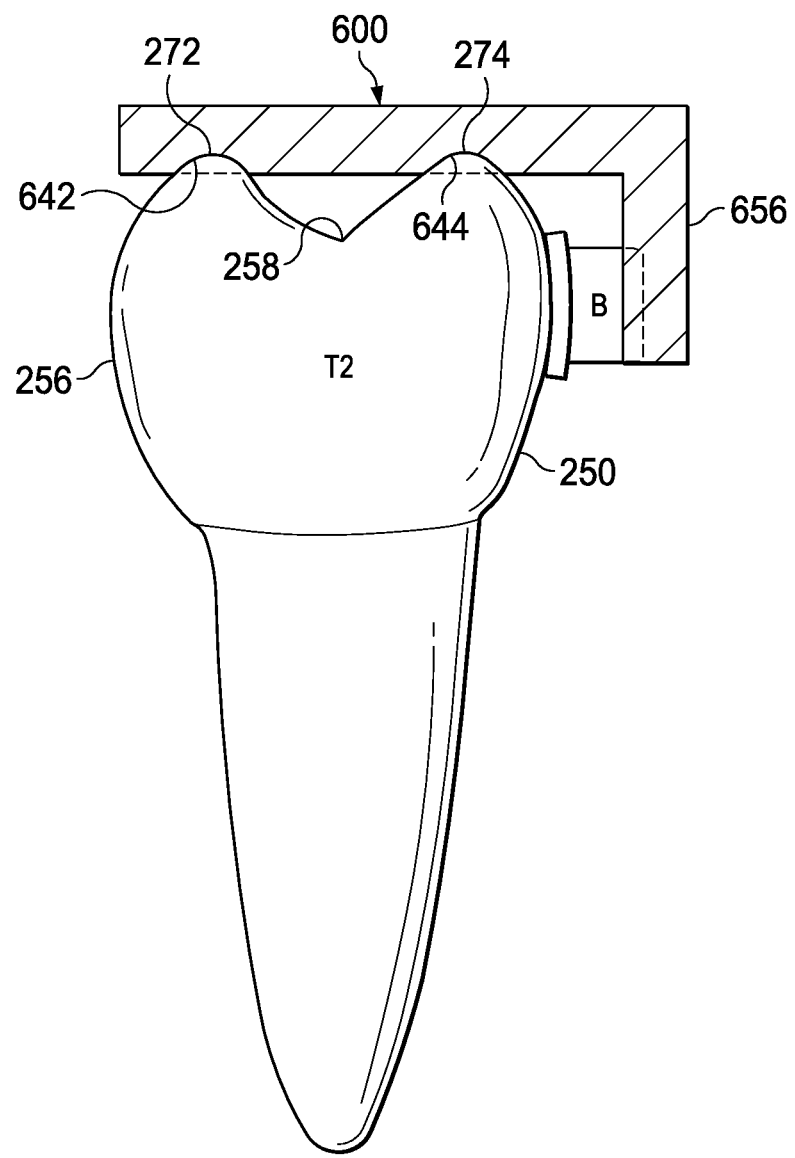

FIG. 6B is a partial cross sectional side view of the second transitional jig and bracket of FIG. 6A.

Figure 7:
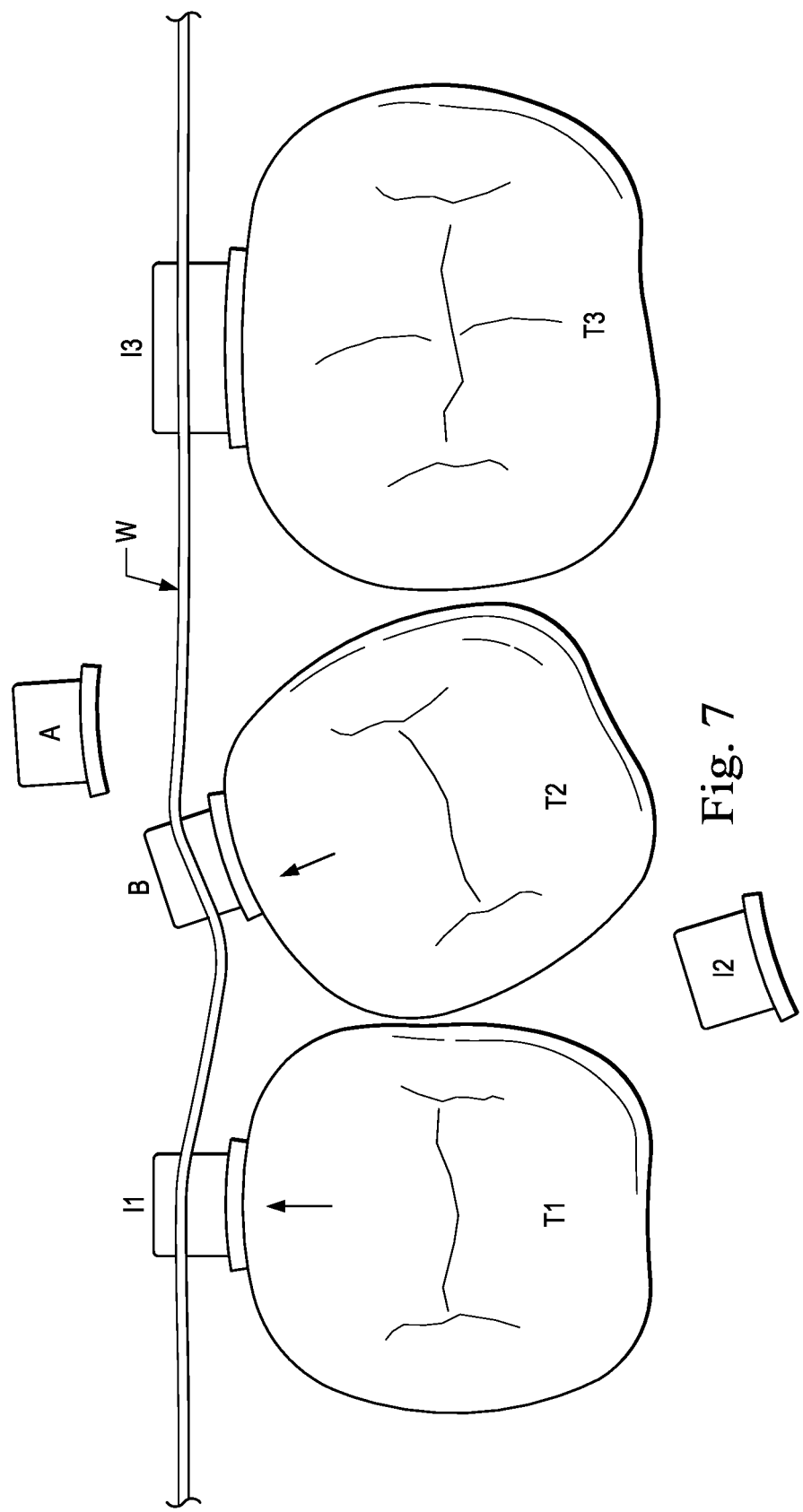

FIG. 7 is a top view of the second transitional bracket of FIG. 6A bonded to the tooth and attached to the wire in a first transitional position.

Figure 8:
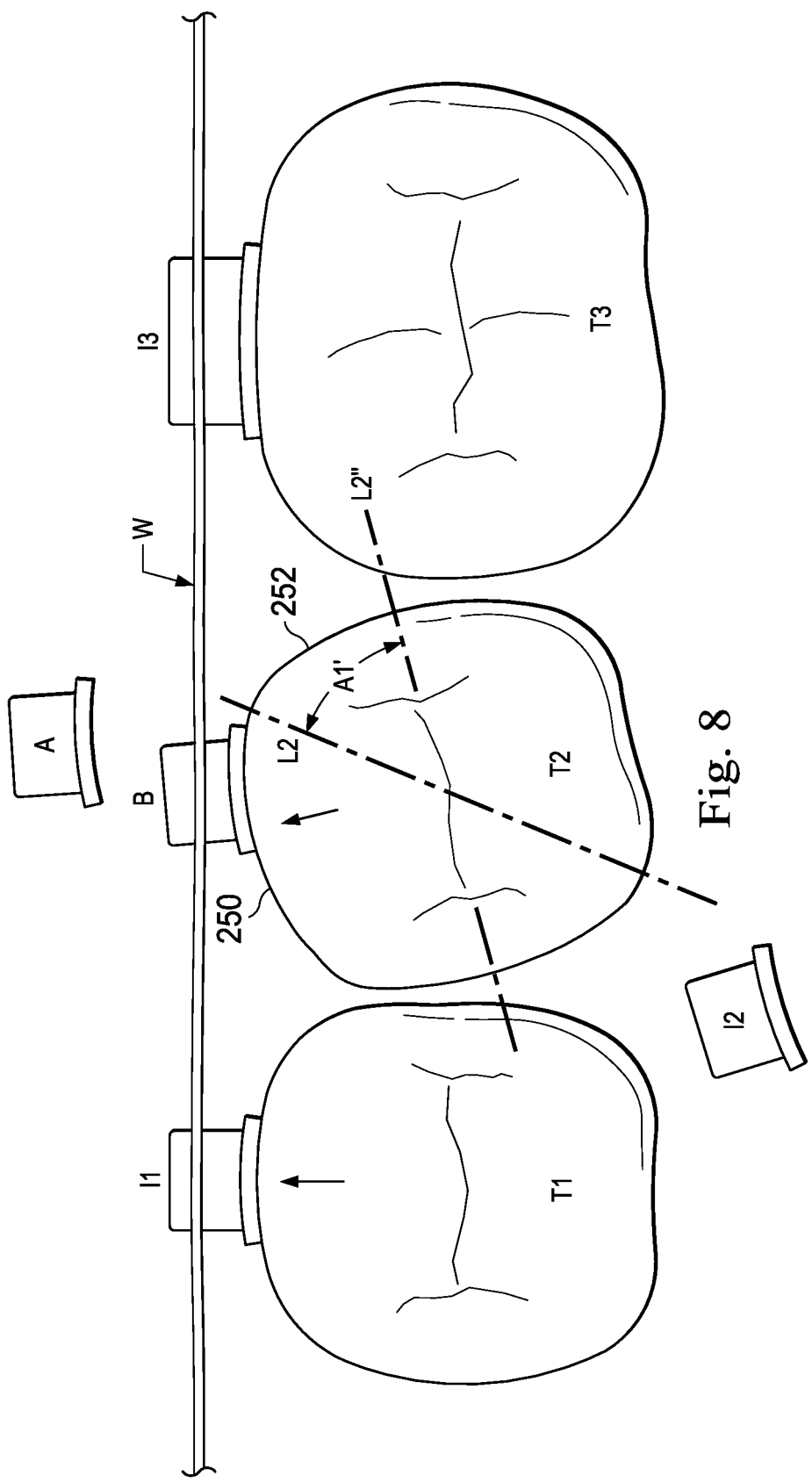

FIG. 8 is a top view of the second transitional bracket of FIG. 6A bonded to the tooth and attached to the wire in a second transitional position.

Figure 9:
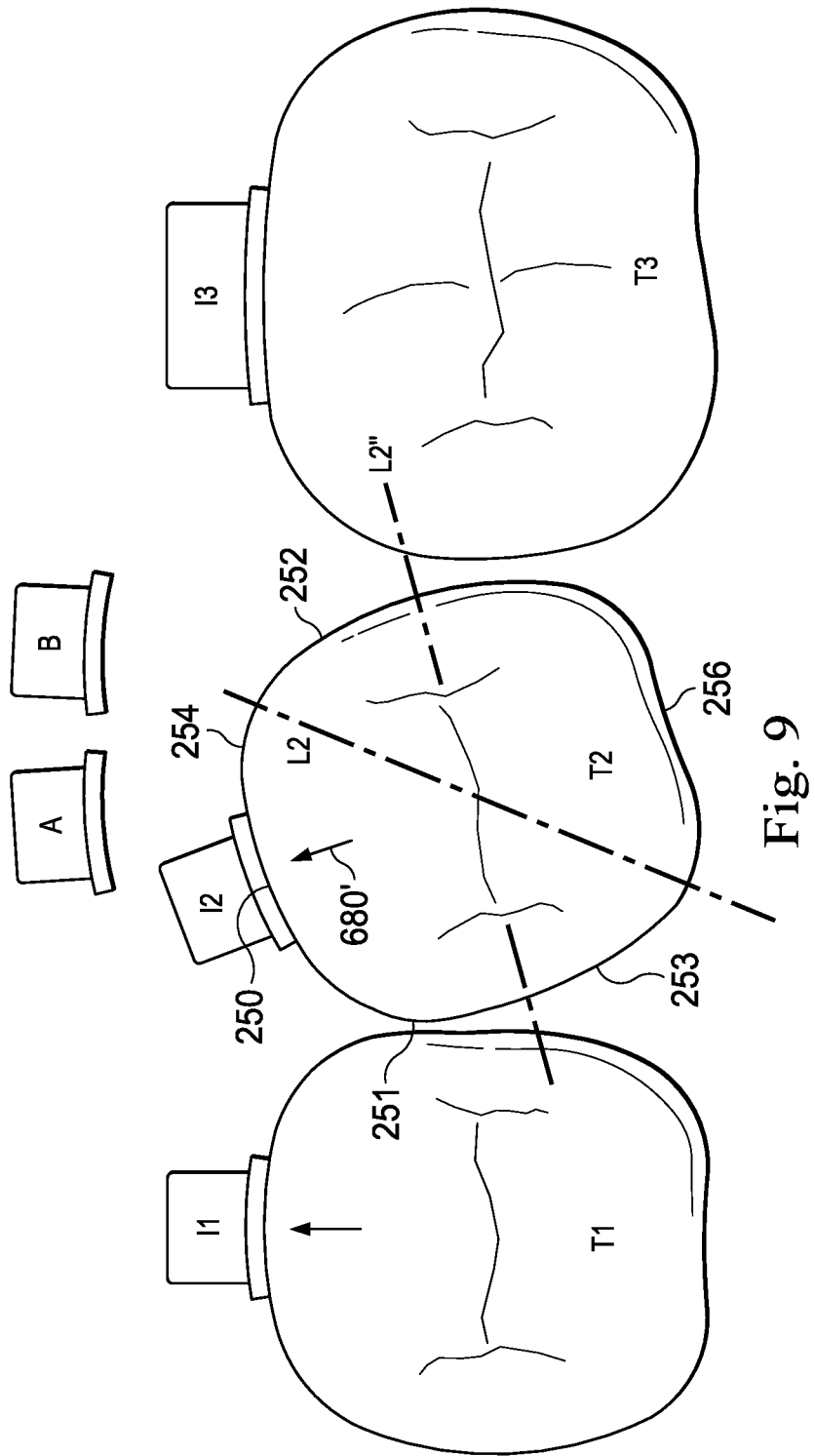

FIG. 9 is a top view of an ideal bracket of FIG. 1 bonded to the tooth in the second transitional position of FIG. 8.

Figure 10:
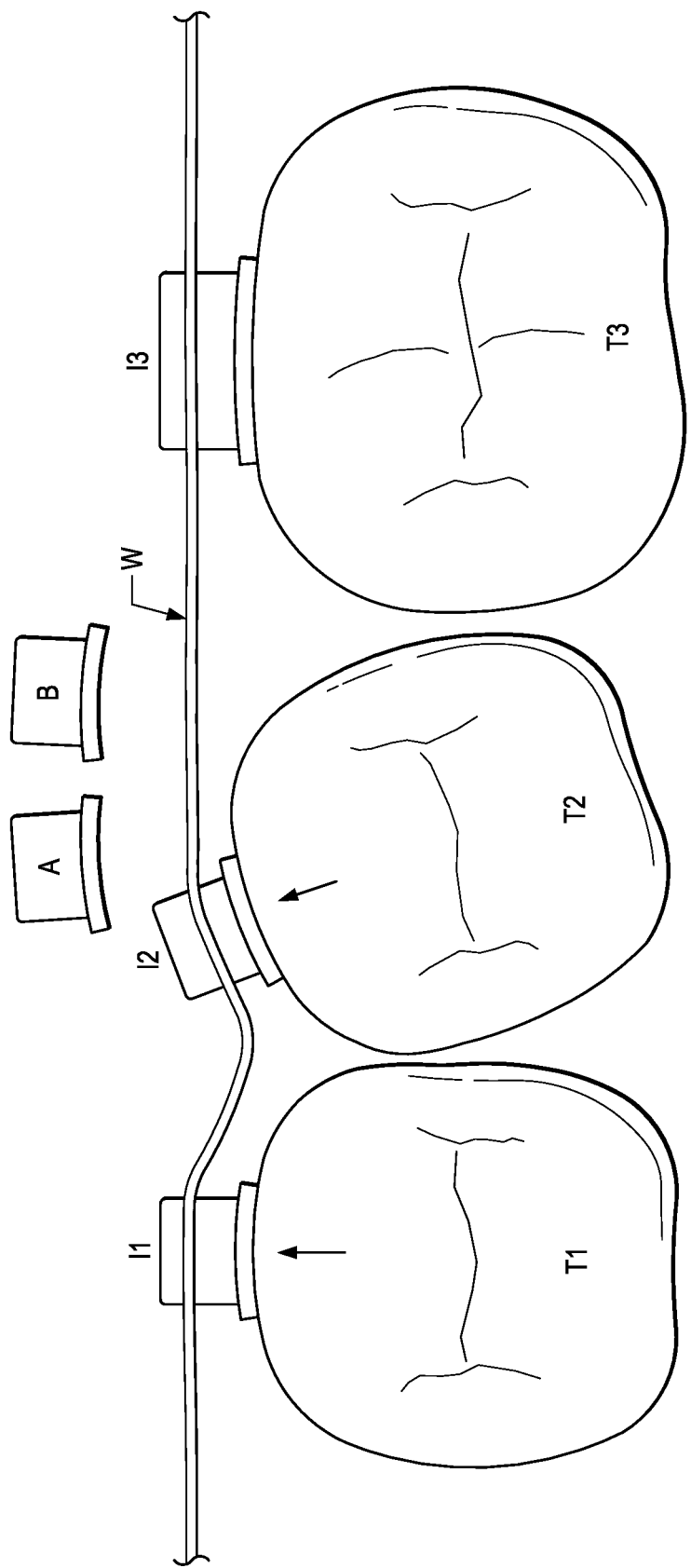

FIG. 10 illustrates the ideal bracket of FIG. 9 attached to the wire.

Figure 11:
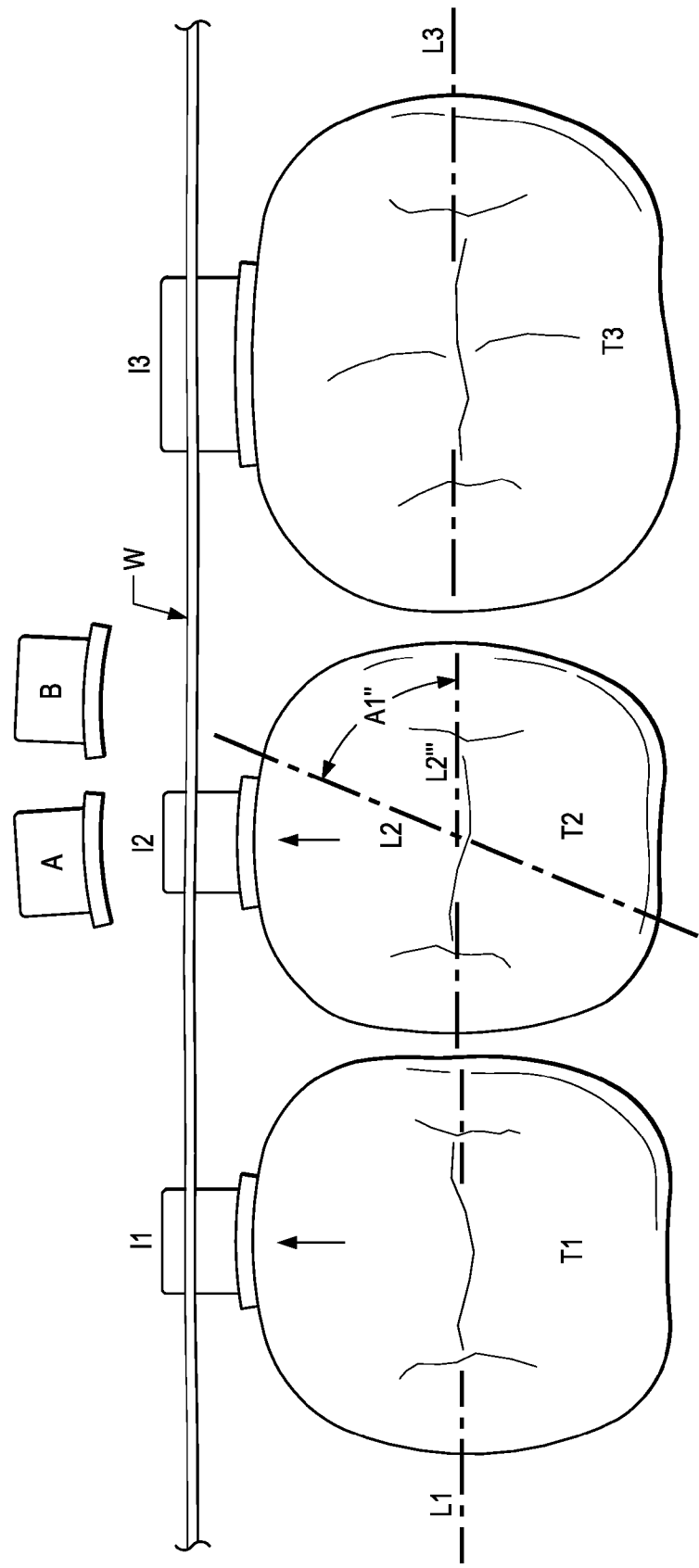

FIG. 11 illustrates the ideal bracket of FIG. 9 with the tooth shown in the finished rotational position.

FIG. 12 is a stylized version of a bracket and transfer jig system for treating a patient's teeth according to one aspect of the present disclosure.

Figure 13:
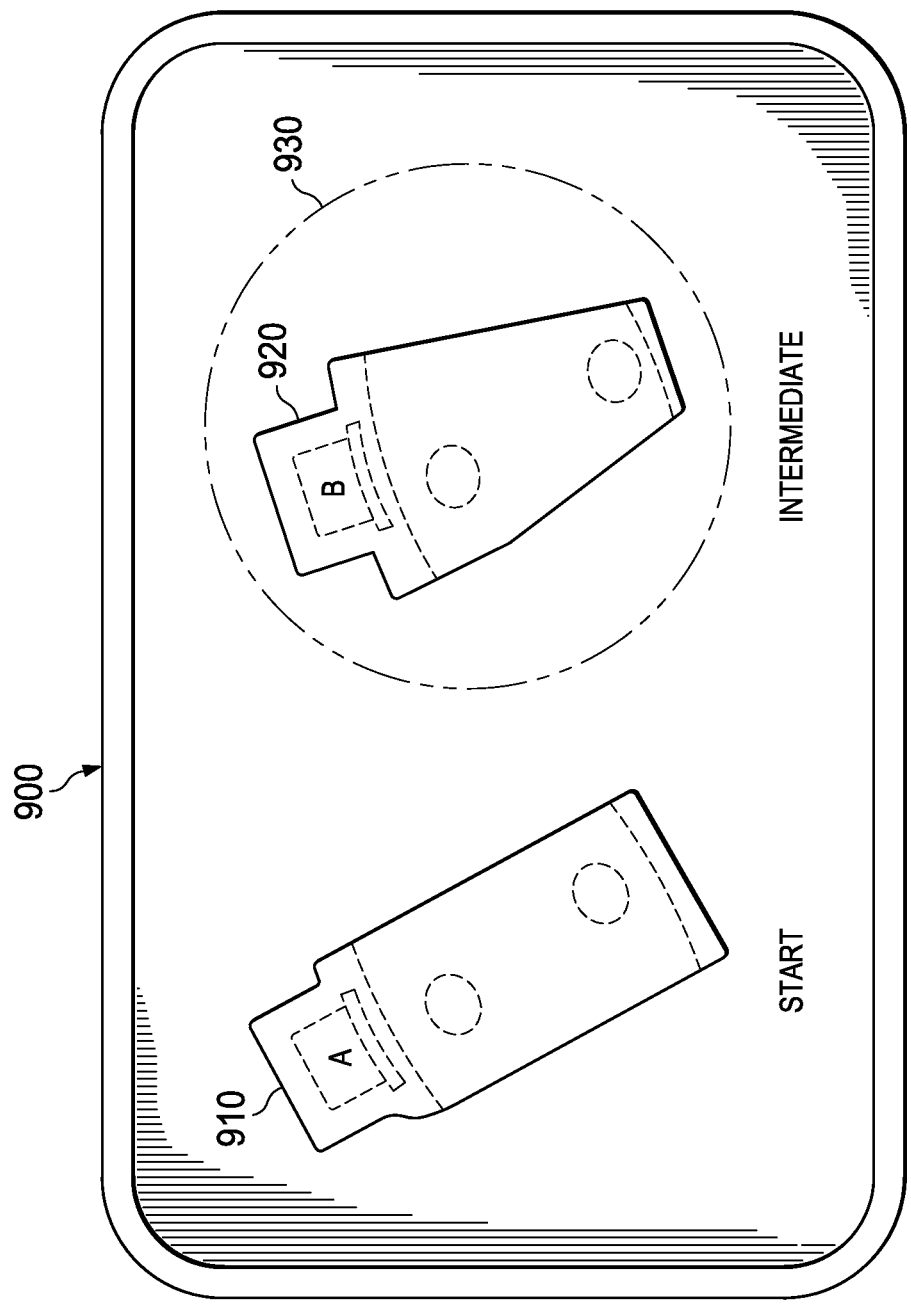

FIG. 13 is an exemplary derotation module associated with the bracket and transfer jig system of FIG. 12 according to another aspect of the present disclosure.

Figure 14:
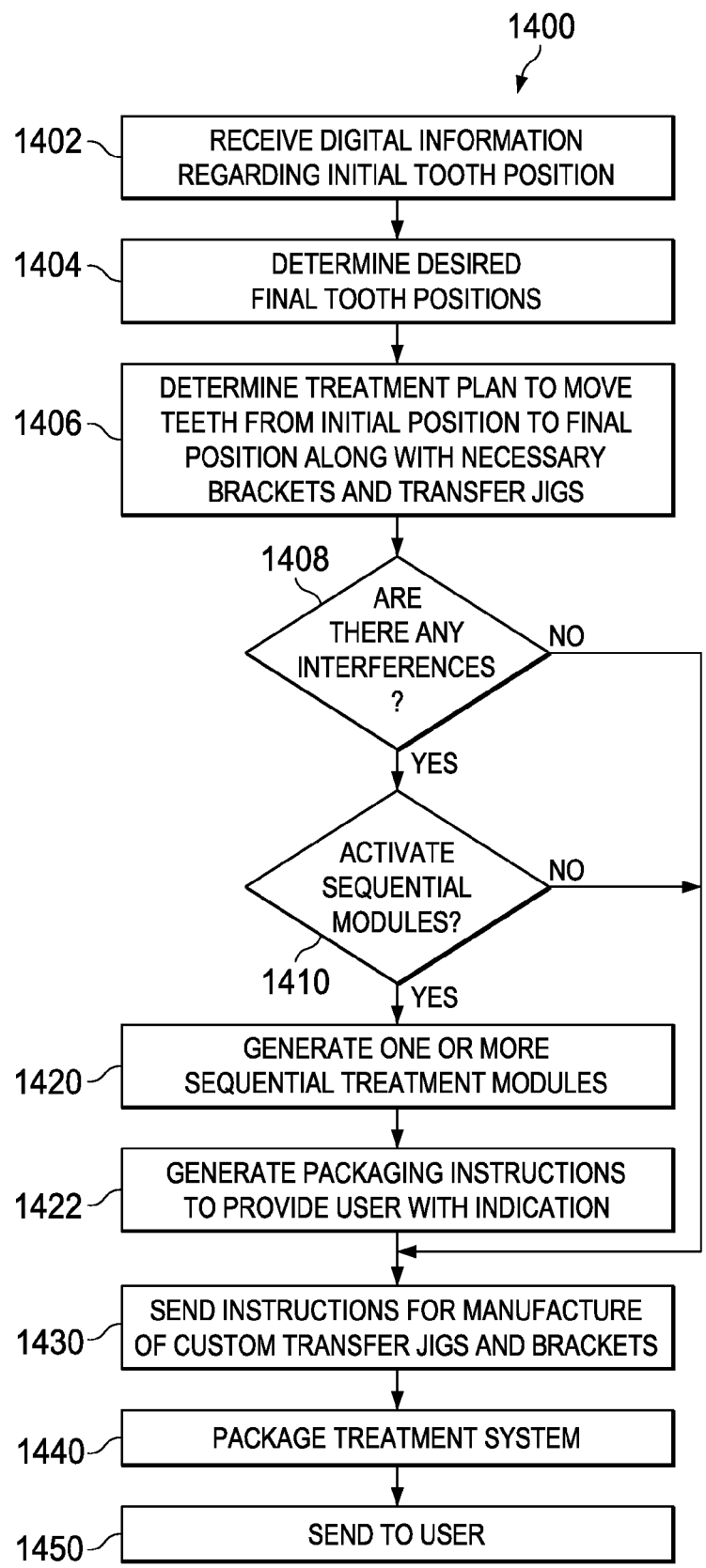

FIG. 14 is a block diagram of a process flow implementing at least one aspect of a computer aided sequential treatment system.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

Referring initially to FIG. 1, there is shown a graphic representation of the output of a computer aided bracketing system treatment plan. Features of such systems are described in the U.S. Pat. Nos. 5,368,478; 6,358,044; 6,846,179; 7,641,473; and 7,869,983 the disclosure of each of with is incorporated by reference herein in their entirety. Stylized images of digitized teeth T1, T2 and T3 are shown in their original starting position. Each tooth T1, T2, and T3 has a longitudinal axis L1, L2, and L3 generally aligned with trough 158, 258 and 358, respectively. Teeth T1 and T3 have generally aligned axes L1 and L3 with facial surfaces 150 and 350, and lingual surfaces 156 and 356 of teeth T1 and T3 each oriented facial and lingually, respectively. As shown in FIG. 1, the axis L2 of tooth T2 is rotationally offset from the axis L1 of the adjacent tooth T1 by an angle A2. In the illustrated embodiment, the angle A2 is approximately 70 degrees, although this angle could range from 15-110 degrees. Given the rotational offset of the tooth T2 with respect to the adjacent teeth, the facial surface 250 is facing tooth T1 while the lingual surface 256 is facing tooth T3. Similarly, the side surface 252 is oriented facially along with the more highly curved transition zone 254 extending between the facial surface 250 and the side surface 252. The side surface 253 opposing the surface 252 is disposed generally lingually in the illustration of FIG. 1 while the lingual surface 256 is substantially facing toward tooth T3.

Existing computer aided orthodontic appliance planning systems utilize the starting position of the digitized teeth to develop a placement plan for a bracket and wire system to move the teeth to a desired finished position. In the illustrated version, the system determines the "ideal position," generally the midpoint, 160, 260, and 370 of the facial surface of each tooth T1, T2 and T3, respectively. The system then assigns a bracket to be placed on the tooth in the ideal position to accomplish the movement to the final position. Based on calculations performed by a processor executing a treatment program, the brackets I1, I2 and I3 are considered the "ideal" brackets to accomplish the tooth movement from the starting position into the final, finished position. In the ideal position, the axis of each ideal bracket intersects the tooth axes L1, L2, and L3, respectively, at a substantially perpendicular angle. For example, in the ideal position 260, the axis LI2 of the ideal bracket I2 for tooth T2 intersects the tooth axis L2 at a substantially perpendicular angle.

However, as shown in FIG. 1, bracket 12 has an overlap zone 230 with adjacent tooth T1. It will be appreciated that the bracket I2 cannot be placed in the ideal position 260 on the facial surface 250 of tooth T2 in the current orientation because there would be interference between the bracket I2 and adjacent tooth T1. Other forms of interference can also be determined by the computer aided design system, such as bracket to tooth, jig to tooth, bracket to gum, and wire to tooth interferences. When such interferences are identified, the proposed computer aided treatment plan must be abandoned in favor of a traditional manually defined treatment plan or the tooth T2 must be manually realigned before the computer aided treatment plan can be applied. In either situation, the healthcare provider must make adjustments to the position of at least tooth T2 based on observation and without the benefit of a computer aided treatment plan that will lead the to the fastest, most accurate correction of the teeth.

Referring now to FIG. 2, there is shown an output of a computer aided treatment plan to move teeth T1, T2 and T3 into a final position. As illustrated, the computer aided treatment plan has determined that based on the angle of rotation A2 of tooth T2, two rotational brackets A and B will be need before the ideal bracket 12 can be applied to at the ideal position central facial surface. Thus, a transitional tooth module has been defined by the system to include three brackets A, B and 12, each being placed at a different angular location on the tooth in relation to axis L2. A description of the system for determining whether a derotation module will be initiated and what the components will is described below in relation to FIG. 14.

As shown in FIG. 2, while there is minimal overlap between bracket B and tooth T1, the system determined that the transfer jig 600 (shown in dashed lines) needed to properly place bracket B created a zone of overlap 602, thus requiring placement of the initial bracket A. The bracket A will be placed at a first offset position on a plane of the tooth T2 with the bracket axis LA intersecting the tooth axis L2 at a first offset angle A3. The first offset angle A3 is an acute angle relative to the tooth axis L2. In the first offset position, at least a portion of a mounting pad 603 of the bracket A is bonded to the side surface 252 and the transition surface 254. The term "offset" is used to describe a bracket position on a surface of the tooth that is offset from the ideal position calculated by the computer aided planning system. As shown in FIG. 3A, the jig needed to place bracket A in the first offset position is configured to avoid a zone of overlap with adjacent teeth.

According to the defined treatment plan illustrated in FIG. 2, the bracket B will then be placed at a second offset location on a plane of the tooth closer to the ideal position with bracket axis LB forming a second offset angle A3' (larger than the first acute angle) with respect to tooth axis L2. The second offset position has the bracket B positioned more facially with a portion of the pad bonded to the facial surface 250 and a portion bonded to the transition surface 254. It will be appreciated that one or more rotational brackets can be used to move the tooth. Further, as illustrated, the centers of the transitional brackets A and B do not align with the center 260 of the facial surface 250. As shown in FIG. 2, the bracket 12 can later be positioned at the ideal position 260 to form a substantially perpendicular angle A3" with the axis L2.

Referring to FIGS. 3A and 3B, there is a shown a further portion of a transitional module according to another aspect of the present disclosure. More specifically, as is known with existing systems, custom designed transfer jigs 400 and 410 are provided to apply the ideal brackets I1 and I3, respectively, to the designated teeth. As shown in FIG. 3A, a transitional transfer jig 420 is shown with the rotational bracket A positioned on tooth T2. The transfer jig 420 is oriented along the direction of arrow 480 with side walls 450 and 452 positioned at a non-orthogonal angle with respect to axis L2. As shown in FIG. 3B, the jig 420 extends across a trough 258 to span the tooth from the side surface 252 to the opposing side surface 253. The jig 420 is maintained in position by the engagement of recesses 442 and 444 with tooth peaks 272 and 274, respectively. In this position, a recessed sidewall portion 454 is positioned adjacent tooth T1 and a front wall 456 is positioned generally facially. The engagement of the transitional jig 420 allows the rotational bracket A to be held in place in the position calculated by the computer aided treatment system as shown in FIG. 2.

FIG. 4 illustrates the rotational bracket A offset position on tooth T2. The bracket A is interconnected with the brackets I1 and I3 via a wire W. The wire W is configured to partially rotate tooth T2. The remaining portions to the sequential treatment brackets B and I2 are shown below T2 and are retained by the orthodontist for later installation on the tooth.

Referring now to FIG. 5, the bracket A is shown aligned along the wire W with the brackets I1 and I3. Tooth T2 has been rotated by an angle of A1 from the initial position at L2 to a first intermediate rotational position L2'. In one embodiment, A1 is in the range of approximately 15-30 degrees. Once the teeth positioning has progressed to the positions shown in FIG. 5, the treatment plan may be continued with the second module of the transitional treatment plan.

Referring now to FIGS. 6A and 6B, the bracket A has been removed from tooth T2. The brackets I1 and I3 remain on teeth T1 and T3, respectively. A second transitional transfer jig 600 is shown with the rotational bracket B positioned on tooth T2. The transfer jig 420 is oriented along the direction of arrow 680 with side walls 650 and 652 positioned at a non-orthogonal angle with respect to axis L2', although the angle of orientation is not less than the angle A2 from FIG. 1.

As shown in FIG. 6B, the jig 600 extends across the trough 258 to span the tooth T2 from the side surface 252 to the opposing side surface 253. The jig 600 is maintained in position by the engagement of the occlusal surfaces or recesses 642 and 644 with the occlusal tooth surfaces or tooth peaks 272 and 274, respectively. In this position, a sidewall portion 654 is positioned adjacent tooth T1 and a front wall 656 positioned generally facially with the bracket B contacting at least a portion of the facial surface 250 of tooth T2. The engagement of the transitional jig 600 allows the intermediate rotational bracket B to be held in place in the offset position calculated by the computer aided treatment system as shown in FIG. 2. The intermediate rotational bracket B may be bonded to tooth T2 in the offset position shown in FIGS. 6A and 6B.

FIG. 7 illustrates the intermediate rotational bracket B positioned on tooth T2. The bracket B is interconnected with the brackets I1 and I3 via the wire W. The wire W is configured to partially rotate tooth T2. The remaining portion of the sequential treatment system, the bracket I2, is shown below T2 and is retained by the orthodontist for later installation on the tooth.

Referring now to FIG. 8, the wire W has effected additional rotation of tooth T2 through bracket B such that longitudinal axis L2" is now offset from the starting longitudinal axis L2 by an angle of A1' (which is larger than the angle A1 of FIG. 5, but is still smaller than the original offset angle A2 of FIG. 1).

Referring now to FIG. 9, tooth T2 has been rotated by the application of rotation module brackets A and B sufficiently to apply the ideal bracket 12 to the facial surface 250 of tooth T2 in the calculated ideal position (e.g., position 260 shown in FIGS. 1-2). In other words, the tooth T2 has been rotated sufficiently to reduce the interferences or areas of overlap enough to allow for the placement of the bracket 12 in the ideal position (e.g., position 260 shown in FIG. 1). As shown, the bracket 12 is positioned substantially in line with arrow 680' which is substantially perpendicular to the axis L2" of tooth T2.

With reference to FIG. 10, the wire W may not be interconnected with the brackets in a traditional fashion to complete the computer generated treatment plan.

As shown in FIG. 11, upon completion of the treatment, the tooth T2 has been rotated through an angle A1" substantially matching the original offset angle A2. Similarly, a longitudinal axis L2' of the tooth T2 is generally aligned with the axis L1 of tooth T1 and the axis L3 of tooth T3. While the illustrated embodiment is shown with substantially linearly aligned teeth for ease of illustration, it will be appreciated that teeth structures in the mouth vary and that often teeth are aligned along a curve or arc rather than in a pure linear fashion. The description of the alignment of teeth is illustrative, it being understood that the rotation of the intermediate tooth to affect the computer aided treatment plan allows final positioning of the teeth in the desired position.

Referring now to FIG. 12, there is shown a treatment system kit 1200 according to another aspect of the present disclosure. More specifically, the treatment system kit 1200 includes a series of brackets and transfer jigs necessary to implement a traditional computer aided tooth correction plan. However, in the illustrated embodiment a cap 1210 covers one of the brackets and transfer jigs. The cap 1210 provides a visual indicator to the user that the underlying bracket and jig should not be used in the initial installation on the teeth. Instead, the user must first apply one or more sequential treatment modules to the tooth of interest before the final treatment bracket positioned under cap 1210 can be applied. As described above, the sequential treatment needed may be a derotation of a tooth, such that the cap is an indicator that rotation sequence has been engaged by the computer aided treatment plan.

Thus, FIG. 12 illustrates a computer designed orthodontic treatment system kit with user indication signaling the need for sequential treatment of at least one tooth. A sequential treatment module package 900 is shown positioned centrally in the packaging of the treatment system. As discussed above, the computer aided design system determines the treatment plan for movement of the teeth including whether any teeth need sequential treatment by one or more preliminary offset brackets before placement of the final, ideal brackets. In the pictured embodiment, the sequential treatment module package 900 includes a series of a sequential treatment modules 910 and 920.

FIG. 13 illustrates an enlarged view of the package 900 having the series of sequential treatment modules 910 and 920 according to at least one aspect of the present disclosure. Although for some patients, only a single treatment module will be needed before sequentially applying the final treatment bracket, the illustrated version includes two pre-final, offset brackets A and B as previously described along with their associated transfer jigs. As set forth above, the brackets and transfer jigs of each module have been computer designed based on imaging of the teeth to provide a custom fit for the tooth at an initial offset starting position for the module 910 and at a calculated intermediate offset position for module 920. In addition, since more than one treatment module is included in the sequential treatment system, a cover 930 is positioned over the intermediate module 920 to indicate to the user to apply the module 910 first and retain the module 920 for later application.

Although the sequential treatment module package 900 is shown positioned within the packaging of the ideal bracket system, it will be appreciated that the modules may be packaged completely separately. In addition, it is contemplated that in an alternative form, the position of the tooth needing sequential treatment may have a layered packaging system such that the user peels away layers to expose the next bracket and jig module needed to affect the desired treatment. Still further, while the description is in relation to derotation of a tooth, it will be appreciated that the description is not limited to any particular tooth misalignment and the general concepts disclosed herein can be applied to other misalignments including partially erupted teeth, baby teeth, and overlapped starting alignments of adjacent teeth or interference between top and bottom teeth.

Referring now to FIG. 14, there is shown a block diagram of an implementation flow diagram 1400 of how the sequential treatment system may be implemented in at least one embodiment. The following description is made in relation to enhancement of existing computer aided treatment systems such as described above and incorporated by reference herein. At step 1402, a computer system receives digitized information representative of the initial tooth positions within the mouth. Often, this information is obtained via a scan of the mouth, although other forms of obtaining such information are contemplated. The computer system then determines the desired final tooth positions at step 1404. At step 1406, the computer system determines the plan for moving each tooth from the initial position to the final position. As part of this determination, the system determines the type of ideal bracket needed for each tooth, its ideal bonding location on the tooth and the shape of a transfer jig necessary to align the bracket with the desired position on the tooth. At step 1408, the system then determines if there are any interferences between the teeth, gums, ideal brackets, jigs or wires at any point during the treatment path. If there are no interferences identified, then the system moves on to sending instructions for manufacturing the custom components in step 1430. If interferences are detected at step 1408, then the system alerts the user at step 1410 and asks whether the system should implement sequential treatment modules to address the identified interferences. The system may be configured such that the system always performs the sequential module without waiting for user input. In the illustrated embodiment, at step 1410 the user indicates whether a computer aided sequential module should be initiated. If no, the system moves to step 1430. If yes, the system moves to step 1420 and generates the necessary sequential treatment modules needed to move at least one tooth into position to receive the ideal bracket system previously identified at step 1406. Although not illustrated, it will be appreciated that the user can approve or reject computer aided design options for the sequential modules and may have access to modify the proposed sequential modules.

Once the sequential treatment modules have been developed, the computer system next determines the package layout or configuration at step 1422 such that the manufacturing portion of the system will provide the sequential treatment system in a unique form to the end user, such as an orthodontist, in a manner that will alert the user to the existence of at least two treatment brackets for a single tooth. The computer aided designs along with packaging information are then forwarded, typically by sending electronic data, at step 1430 to the manufacturing system. The components of the system are selected from inventory or custom manufactured as necessary and then packaged in step 1440 according to the packaging instructions. The complete sequential treatment system, including sequential modules, may then be shipped to the end user at step 1450. In an alternative form, only the brackets and jigs needed for the initial installation are shipped initially with the sequential brackets following separately based on the timing determined by the computer aided treatment plan.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method for computer aided tooth alignment correction, comprising:
    receiving digital information regarding initial teeth positions;
    determining desired final teeth positions and a treatment plan of ideal brackets, ideal jigs for placing the ideal brackets in ideal positions on the teeth and wires for achieving the final teeth positions;
    identifying whether there will be an interference between at least one of the ideal brackets, jigs, and wires and at least one of teeth and gums; and
    upon identification of the interference, generating one or more sequential treatment modules, each comprising an offset bracket and an offset jig for placing the offset bracket on a specified tooth in a position offset from the ideal position for the specified tooth, to address the identified interference prior to application of the ideal bracket with the ideal jig in the ideal position to the specified tooth.

2. The method of claim 1, wherein the interferences comprise at least one zone of overlap.

3. The method of claim 2, wherein the interferences comprise at least one area of overlap between at least one of the ideal brackets and an adjacent tooth.

4. The method of claim 1, further including determining an original offset angle for each tooth.

5. The method of claim 1, further including packaging the ideal brackets and jigs along with the sequential treatment module.

6. The method of claim 1, wherein said generating includes developing a first offset bracket configuration and a corresponding first offset jig configuration for placement of the first offset bracket on the specified tooth at a first offset position from the ideal position.

7. The method of claim 6, wherein said developing includes calculating a first offset angle for the first offset bracket.

8. The method of claim 6, further including developing a second offset bracket configuration and a corresponding second offset jig configuration for placement of the second offset bracket on the tooth at a second offset position.

9. The method of claim 8, wherein said developing includes calculating a second offset angle for the second offset bracket.

10. A method, comprising:
receiving, at a computer system, digitized information representing initial tooth positions of a plurality of teeth in a patient's mouth;
determining, by a processor of the computer system, a desired final position for the plurality of teeth;
determining, by the processor, a treatment plan for moving each tooth from the initial tooth positions to the desired final position for the teeth, wherein the treatment plan includes an ideal bracket and an ideal jig to place the ideal bracket in an ideal bonding location at each tooth, the ideal bonding location comprising a midpoint of a facial surface of each tooth;
detecting, by the processor, an interference between at least one of an ideal bracket in an ideal bonding location and an ideal jig for a specific tooth, and at least one of another tooth from among the plurality of teeth and the patient's gums during the treatment plan; and
determining, by the processor, at least one sequential bracket and corresponding sequential jig configured to place the sequential bracket in a location on the specific tooth different from the ideal bonding location to reduce the detected interference.

11. The method of claim 10, further comprising:
determining, by the processor, a package layout that includes the ideal bracket and ideal jig for each tooth from among the plurality of teeth, wherein the package layout includes an identifier to alert a user that at least two brackets and at least two jigs exist for the specific tooth.

12. The method of claim 11, wherein the identifier comprises a cap that covers the ideal bracket and the ideal jig for the specific tooth, the cap visually indicating that the underlying ideal bracket and the ideal jig are not to be used in an initial installation on the specific tooth.

13. The method of claim 11, further comprising:
sending, by the processor, the treatment plan including the determined at least one sequential bracket and corresponding sequential jig together with the package layout to a manufacturing system to manufacture and package a treatment system.

14. The method of claim 13, further comprising:
instructing the manufacturing system to ship the manufactured treatment system, including the manufactured at least one sequential bracket and corresponding sequential jig, to the user at the same time.

15. The method of claim 10, wherein the determining the at least one sequential bracket and corresponding sequential jig comprises:
calculating a first offset angle for the sequential bracket from the ideal bonding location; and
determining a jig configuration for the sequential jig that places the sequential bracket at the calculated first offset angle on the specific tooth.

16. A method, comprising:
determining, by a processor of a computer system, a desired final position for a plurality of teeth, wherein each tooth comprises a longitudinal axis that is perpendicular to a facial surface of the tooth;
determining, by the processor, a treatment plan for moving the plurality of teeth from initial tooth positions to the desired final position for the plurality of teeth, the treatment plan comprising an ideal jig to place an ideal bracket in an ideal bonding location at each tooth at the facial surface of each tooth;
identifying, by the processor, an interference at an ideal bonding location of an identified tooth, the interference being between at least one of an ideal bracket for the identified tooth, an ideal jig for the identified tooth, and a wire, and at least one of an adjacent tooth from among the plurality of teeth and gums; and
generating, by the processor in response to the identifying, a transitional tooth module comprising at least one rotational bracket and a corresponding transfer jig configured to place the rotational bracket in a location on the identified tooth different from the ideal bonding location.

17. The method of claim 16, further comprising:
calculating an offset angle for the rotational bracket, the offset angle being an acute angle relative to the longitudinal axis of the identified tooth; and
determining a jig configuration for the transfer jig that places the rotational bracket at the calculated offset angle on a side surface of the identified tooth.

18. The method of claim 17, wherein the at least one rotational bracket comprises a first rotational bracket with a calculated first offset angle and the corresponding transfer jig comprises a first transfer jig, the method further comprising:
generating, as part of the transitional tooth module, a second rotational bracket and a second transfer jig.

19. The method of claim 18, further comprising:
calculating a second offset angle for the second rotational bracket, the second offset angle being an acute angle relative to the longitudinal axis that is greater than the first offset angle,
wherein the first rotational bracket with corresponding first transfer jig is designed for use before the second rotational bracket with corresponding second transfer jig.

20. The method of claim 16, wherein the identifying further comprises:
identifying an overlap between the ideal bracket on the identified tooth and an adjacent tooth from among the plurality of teeth.

* * * * *